(12) United States Patent
Ying et al.

(10) Patent No.: US 8,263,135 B2
(45) Date of Patent: Sep. 11, 2012

(54) PROCESS FOR ISOLATING BIOMATERIAL FROM TISSUE AND AN ISOLATED BIOMATERIAL EXTRACT PREPARED THEREFROM

(76) Inventors: Jackie Y. Ying, Nanos (SG); Shona Pek, Nanos (SG)

( * ) Notice: Subject to any disclaimer, the term of this patent is extended or adjusted under 35 U.S.C. 154(b) by 934 days.

(21) Appl. No.: 11/662,443

(22) PCT Filed: Sep. 9, 2004

(86) PCT No.: PCT/SG2004/000289
§ 371 (c)(1),
(2), (4) Date: Jan. 22, 2008

(87) PCT Pub. No.: WO2006/028415
PCT Pub. Date: Mar. 16, 2006

(65) Prior Publication Data
US 2008/0188642 A1 Aug. 7, 2008

(51) Int. Cl.
*A61K 35/36* (2006.01)
*A61K 35/12* (2006.01)
(52) U.S. Cl. .................. 424/574; 424/572; 424/529
(58) Field of Classification Search .................. None
See application file for complete search history.

(56) References Cited

U.S. PATENT DOCUMENTS

| | | | | |
|---|---|---|---|---|
| 4,193,813 | A * | 3/1980 | Chvapil | 106/122 |
| 4,849,232 | A * | 7/1989 | Baker et al. | 426/92 |
| 4,948,540 | A | 8/1990 | Nigam | |
| 4,970,298 | A * | 11/1990 | Silver et al. | 530/356 |
| 6,337,389 | B1 | 1/2002 | Wolfinbarger, Jr. | |
| 6,969,523 | B1 | 11/2005 | Mattern et al. | 424/423 |
| 7,175,852 | B2 * | 2/2007 | Simmoteit et al. | 424/423 |
| 7,445,793 | B2 * | 11/2008 | Niwa et al. | 424/426 |
| 2003/0118982 | A1 * | 6/2003 | Yamamoto et al. | 435/1.3 |
| 2004/0121943 | A1 | 6/2004 | Hsu | |
| 2005/0107286 | A1 * | 5/2005 | Uemura et al. | 514/7 |

FOREIGN PATENT DOCUMENTS

| | | |
|---|---|---|
| EP | 0 284 789 | 10/1988 |
| EP | 552576 | 1/1992 |
| FR | 2806415 | 9/2002 |
| GB | 2116978 | 10/1983 |
| RU | 1787010 | * 1/1993 |
| RU | 2076718 | * 4/1997 |
| WO | WO 02/62404 | 8/2002 |
| WO | WO 02/102831 | 12/2002 |

OTHER PUBLICATIONS

Becker, et al., "Cyanogen bromide peptides of the rabbit collagen a1-chain," *FEBS Letters* 27(1):85-88 (1972).
Bornstein, M.B., "Reconstituted rattail collagen used as substrate for tissue cultures on coverslips in Maximow slides and roller tubes," *Lab Invest.*, 7(2):134-137 (1958).
Ehrmann and Gey, "The growth of cells on a transparent gel of reconstituted rat-tail collagen," *National Cancer Inst. J.* 16:1375-1403 (1956).
Komjathy, L., "An Overview of the Lyophilization Process and Looking Toward the Future: End Point Determination through Process Analytical Technology (PAT)", Directed Research under professor Henry Wang, Pharmaceutical Engineering, University of Michigan, downloaded from http://www-personal.engin.umich.edu/~lkomjath/lyopat.html. (Apr. 25, 2003).
Li and Shi, "Formation and characteristics of an artificial dermis—collagen-chondroitin-6-sulfate membrane," *Sheng Wu Yi Xue Gong Cheng Xue Za Zhi* (*Journal of Biomedical Engineering*), abstract (article in Chinese) 16(2):151-153 (1999).
Nagai, "Isolation of Collagen From Fish Waste Material—Skin, Bone and Fins," Food Chemistry, 2000, pp. 277-281, vol. 68.

* cited by examiner

*Primary Examiner* — Christopher R. Tate
(74) *Attorney, Agent, or Firm* — McDermott Will & Emery LLP

(57) ABSTRACT

A process for isolating a biomaterial extract from tissue is disclosed. The process comprises the step of contacting the tissue with an extracting solution so as to extract a biomaterial into solution. A solution containing the biomaterial extract is separated before being freeze-dried at a rate sufficient to enable the biomaterial to be isolated. The examples relate to the extraction of collagen from skin or hide using an acetic acid solution as the solvent.

11 Claims, 1 Drawing Sheet

PROCESS FOR ISOLATING BIOMATERIAL FROM TISSUE AND AN ISOLATED BIOMATERIAL EXTRACT PREPARED THEREFROM

TECHNICAL FIELD

The present invention relates to a process for isolating and purifying a biomaterial from tissue and a biomaterial extract prepared therefrom. More particularly the present invention is directed to a process for extracting and purifying a Type 1 collagen extract.

BACKGROUND OF THE INVENTION

Collagen is a major structural protein of connective tissue such as skin, tendon, cartilage and bone. Type 1 collagen forms the major portion of collagen of both soft (skin, tendon) and hard (bone, dentine) connective tissue. Collagen is typically extracted from the skin of animals, such as rat and rabbit. The collagen that is extracted can be used as a coating to new materials or incorporated in a material so as to make the material more biocompatible. Because of its good mechanical properties, biocompatibility, biodegradability, bioavailability, its action on cell development, and hemostatic power, collagen has been used in many medical, veterinary, cosmetic, food, pharmaceutical, biomedical, biotechnological, dental, surgical, dermatological, neurological, orthopedic, ophthalmic, urological and vascular applications. For example, collagen has been used in implants, transplants, organ replacements, tissue equivalents, arterial vessel replacements, hemostatic agents, drug delivery matrices, endodontic therapy, cell culture supports, vitreous replacements, plastic, reconstructive and cosmetic surgery, surgical sutures and surgical dressings.

Various methods have been used for extracting and purifying collagen. Existing methods of collagen extraction and purification typically include extraction from animals using multi-step chemical and mechanical processes, such as described in Ehrmann, R. L., and Gay, G. O., National Cancer Inst. J. 16:1374-1403 and Bornstein, M. B., Lab. Invest, 7:134-137, 1958.

Such methods typically include chemical washes and extractions, filtering, vacuum filtration, decantation, enzyme extraction, salt precipitation, crosslinking reactions and dialysis.

Conventional processes for extracting and purifying collagen, are typically complex, costly and suffer from the disadvantage that the structure of collagen can be modified/denatured by the process. Collagen undergoes glass transition at temperatures as low as 50-60° and if the chemical process used causes the collagen to pass through this glass transition, the physical structure of the collagen can be disrupted. In addition, many extraction methods involve the use of an alkaline metal/metal salt or sodium acetate/hydroxide to precipitate the collagen. Such agents are harsh agents and may cause modification or damage of the collagen. Alternative processes use proteases or enzymes to digest collagen. Proteases and enzymes are typically expensive and can result in alteration and damage to the collagen.

Accordingly, there is a need to provide a simpler method for extracting and purifying collagen.

Object of the Invention

It is an object of the present invention, at least in preferred embodiments, to overcome or substantially ameliorate at least one of the above disadvantages. It also an object of the present invention, at least in preferred embodiments, to provide an improved process for purifying and extracting collagen.

SUMMARY OF THE INVENTION

According to a first aspect of the present invention, there is provided a process for isolating a biomaterial extract from tissue comprising:
 contacting the tissue with an extracting solution so as to extract a biomaterial into solution;
 separating a solution containing the biomaterial extract; and
 freeze-drying the separated solution at a rate sufficient to enable the biomaterial to be isolated.

According to a second aspect of the present invention, there is provided a process for isolating a biomaterial extract from tissue comprising:
 contacting the tissue with an extracting solution so as to extract a biomaterial into solution;
 separating a solution containing the biomaterial extract; and
 freeze-drying the separated solution at a rate of about 0.1° C./min to 50° C./min to enable the biomaterial to be isolated.

According to a third aspect of the present invention, there is provided a biomaterial extract prepared by the process of the first or second aspect of the present invention.

Definitions

The following definitions are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

The term "isolated" or "purified" means that the material in question has been removed from its host, and associated impurities reduced or eliminated. Essentially, it means an object species is the predominant species present (ie., on a molar basis it is more abundant than any other individual species in the composition), and preferably a substantially purified fraction is a composition wherein the object species comprises at least about 30 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

All the references cited in this application are specifically incorporated by reference are incorporated herein in their entirety.

In the context of this specification, the term "biomaterial" refers to any material which is suitable for introduction into a living organism such as a mammal including a human. The biomaterial is suitably non-toxic and bioabsorbable when introduced into a living organism and any degradation products of the biomaterial are also suitably non-toxic to the organism.

BRIEF DESCRIPTION OF THE DRAWINGS

A preferred form of the present invention will now be described by way of example with reference to the accompanying drawings wherein.

DETAILED DESCRIPTION OF PREFERRED EMBODIMENTS

Figure 1:
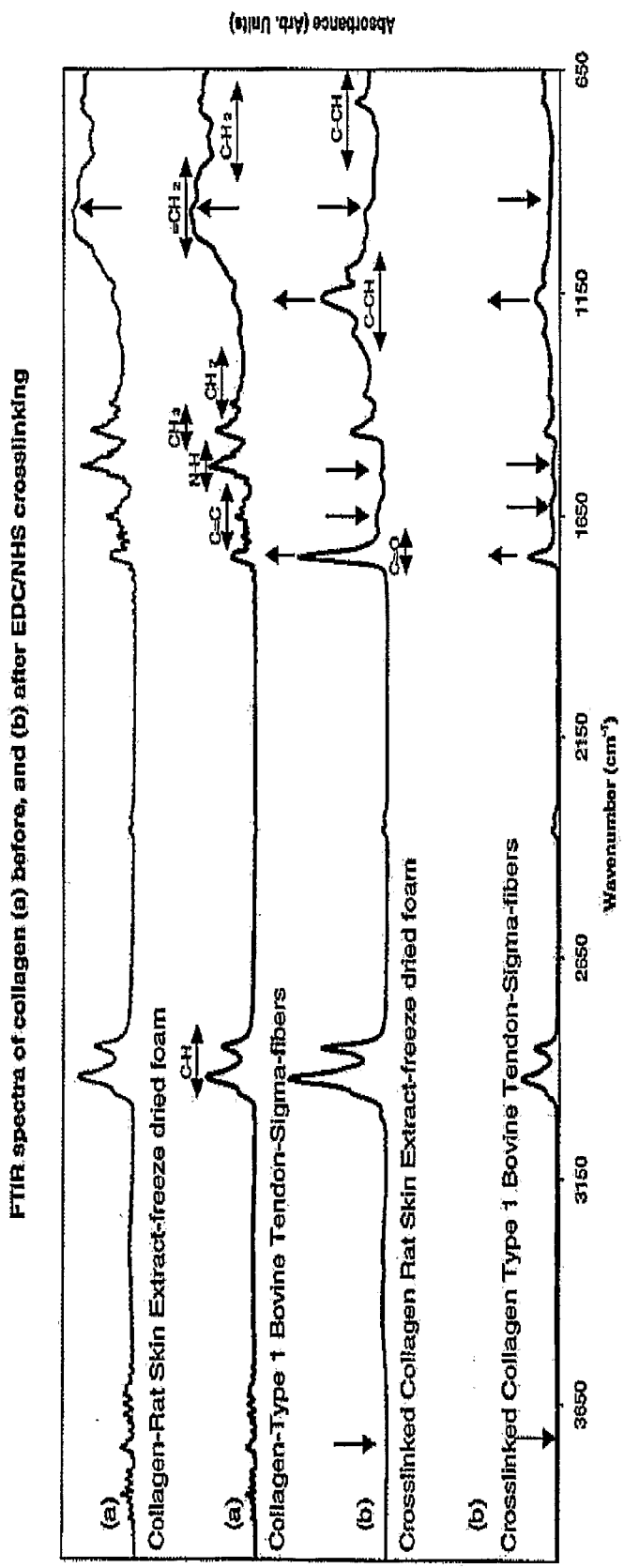
FIG. 1 is a Fourier Transform Infrared Spectra of a collagen product of the present invention prior to and after cross-linking together with that of an uncross-linked and cross-linked commercial product

There is provided a process for isolating and purifying a biomaterial extract from tissue. The process comprises contacting the tissue with an extracting solution so as to extract a biomaterial into solution followed by separating a solution containing the biomaterial extract and freeze-drying the separated solution at a rate sufficient to enable the biomaterial to be isolated.

The biomaterial may be any biomaterial which can be extracted from biological tissue. In one embodiment the biomaterial may be a material extracted from biological tissue such as fetal tissue, skin/dermis, muscle or connective tissue including bone, tendon, ligament or cartilage. In one embodiment the biomaterial may be extracted from skin. In one embodiment the tissue may be animal skin. In one embodiment the skin may be skin of a rat or rabbit. In one embodiment the biomaterial may be a biopolymer. In one embodiment the biomaterial may be selected from substances such as proteins, peptides, polysaccharides and other organic substances. For example the biomaterial may be selected from one or more of growth factors; extracellular matrix proteins, such as fibronectin, laminin, vitronectin, tenascin, entactin, thrombospondin, elastin, gelatin, collagen, fibrillen, merosin, anchorin, chondronectin, link protein, bone sialoprotein, osteocalcin, osteopontin, epinectin, hyaluronectin, undulin, epiligrin and kalinin, proteoglycans such as decorin, dermatin sulfate proteoglycans, keratin, keratin sulfate proteoglycans, aggrecan, chondroitin sulfate proteoglycans, heparin sulfate proteoglycans, biglycan, syndecan, perlecan, serglycin, glycosaminoglyeans such as heparin sulfate, chondroitin sulfate, dermatin sulfate, keratin sulfate or hyaluronic acid; polysaccharides such as heparin, dextran sulfate, chitin, alginic acid, pectin or xylan, polyvinyl alcohol, cytokines, glycosides, glycoproteins, polypyrroles, albumin, fibrinogen, or a phospholipid.

In one embodiment the biomaterial may be collagen. In one further embodiment the collagen may be selected from the group consisting of collagen Type I, collagen Type II, collagen Type III, collagen Type IV, collagen Type V, collagen type VI, collagen Type VII, collagen Type VIII, collagen Type IX, collagen Type X, collagen Type XI, collagen Type XII, collagen Type XIII, collagen Type XIV, or mixtures thereof. In one embodiment the collagen may be Type 1 collagen.

Sources of biomaterial include both land and marine vertebrates and invertebrates including a mammal, marsupial, a human, a non-human primate, murine, bovine, ovine, equine, caprine, leporine, avian, feline, porcine or canine. In one embodiment the biomaterial may be sourced from a mammal or marsupial such as a human, pig, cow, sheep, deer, goat, horse, donkey, hare, rat, mouse, rabbit, kangaroo, wallaby or camel. Suitably the source of biomaterial may be skin from animals used in in vivo studies. The skins may be freshly obtained or may be stored, for example, frozen, prior to use.

In one embodiment the tissue may be sterilized/dehydrated prior to extracting the biomaterial. When skin is used, hair on the skin may be removed prior to use. Sterilization/dehydration may be achieved by contacting the tissue with an alcoholic solution for up to about two weeks, alternatively up to about 1 week, alternatively about 1, about 2, about 3, about 4, about 5, about 6, about 7, about 8, about 9, about 10, about 11, about 12 or about 13 days. Suitably the alcohol may be ethanol however other straight or branched chain $C_1$-$C_{15}$ alcohols or aromatic alcohols may be used including methanol, isopropanol, butanol, tert-butanol, pentanol, cyclohexanol, hexanol, thymol or benzyl alcohol.

In one embodiment the tissue may be chopped or minced into smaller pieces prior to extraction or sterilization. The tissue may be chopped or minced by use of a mincer, grinder, food processor or other mechanical or electrical cutting device. In one embodiment the tissue may be cut into micrometer to centimeter size (for example 1 micrometer to 10 cm in size). For example the tissue may be cut up into pieces of about 1 to about 3 mm in size.

In one embodiment, the biomaterial may be extracted from the tissue by immersing or dipping the tissue into an extracting solution. In another embodiment the tissue may be sprayed or painted with an extracting solution. In one embodiment the biomaterial may be extracted from the tissue with stirring. The solution may be stirred at a speed from 0 to about 2000 rpm, for example about 100 rpm, about 200 rpm, about 300 rpm, about 400 rpm, about 500 rpm, about 600 rpm, about 700 rpm, about 800 rpm, about 900 rpm, about 1000 rpm, about 1100 rpm, about 1200 rpm, about 1300 rpm, about 1400 rpm, about 1500 rpm, about 1600 rpm, about 1700 rpm, about 1800 rpm, about 1900 rpm or about 2000 rpm. In one embodiment the solution is stirred at about 700 rpm.

In one embodiment the extracting solution is an acidic solution. In one embodiment the acidic solution may be an acetic acid solution, suitably a 1:1000 acetic acid solution, the ratio being with respect to water. In one embodiment the water may be deionized water. Other acids may be used, such as organic or inorganic acids including citric acid, pyruvic acid, lactic acid, formic acid, tartaric acid, sorbic acid, sulfuric acid, hydrochloric acid, trifluoroacetic acid, triflic acid, phosphoric acid, pyruvic acid, ascorbic acid or propanoic acid. In one embodiment the acid may be diluted so as to prevent denaturation and damage of the biomaterial. The concentration range of the acid used is dependent on the acid used. Typically less than about 0.8M acid may be used. For example for acetic acid, up to about 0.5M acid may be used, for hydrochloric acid up to about 0.01 M acid can be used. Depending on the acid, about 0.01 M, about 0.02 M, about 0.03 M, about 0.04 M, about 0.05 M, about 0.06 M, about 0.07 M, about 0.08 M, about 0.09 M, about 0.1 M, about 0.2 M, about 0.3 M, about 0.4 M, about 0.5 M, about 0.6 M, about 0.7

M or about 0.8 M acid may be used. The acidic solution may be formed using acidic salts/salt buffers. In one embodiment the pH of the acidic solution may be from about 2 to 6, for example a pH of about 2, about 3, about 4, about 5 or about 6. In one embodiment the pH of the acidic solution is about 4.

In another embodiment the biomaterial may be extracted with or without stirring using a pH neutral salt solvent, for example 0.1 M sodium chloride and 0.05 Tris at a pH of about 7.5. In another embodiment the biomaterial may be extracted with or without stirring using an acidic solution containing enzymes, for example 0.5M acetic acid and pepsin (1:10 w/w).

In one embodiment the extracting solution may be an organic acid buffer. The organic acid buffer may be an acetic acid buffer, citric acid buffer, pyruvic acid buffer, lactic acid buffer or formic acid buffer. In another embodiment the extracting solution may contain an alkali or alkaline metal salt. In one embodiment the buffer may be adjusted to a pH of from about 2 to about 6. For example, a pH of about 2, about 3, about 4, about 5 or about 6 may be used. For example the buffer may be adjusted with sodium acetate, sodium citrate, sodium pyruvate, sodium hydroxide, sodium bicarbonate, sodium carbonate or potassium salts.

In another embodiment the extracting solution may be a Tris-HCl buffer or alkali-containing buffer system, such as a potassium carbonate-containing, phosphate-containing, nitrogen-, ammonium- or sulfate containing buffer with a suitable pH value.

When enzymes are present in the extracting solution, the enzymes may be proteolytic enzymes. Examples of enzymes include those sold under the trade names ESPERASE®, ALCALASE®, DURAZYM®, SAVINASE® (all by Novo Industries A/S of Denmark) or MAXATASE®, MAXACAL®, PROPERASE®, MAXAPEM® (all by Gist-Brocades), or pepsin. In one embodiment the enzyme is pepsin.

In one embodiment the tissue may be contacted with the extracting solution in a ratio from about 10 to about 200 g of tissue per liter of extracting solution.

In one embodiment the tissue may be contacted with the extracting solution for up to about 14 days, typically from about 4 to about 14 days. Shorter or longer times may be used. For example less than about 30 minutes to a number of weeks. For example about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 hours, about 2, about 3, about 4, about 5, about 6, about 7, about 8, about 9, about 10, about 11, about 12, about 13, about 14, about 15, about 16, about 17, about 18, about 19, about 20 or about 21 days. The amount of biomaterial solubilised typically increases with the length of stirring time. In one embodiment the biomaterial may be extracted at room temperature and pressure. In another embodiment the biomaterial may be extracted at a temperature between about 0 and about 40° C. For example the temperature may be about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39 or about 40° C. In one embodiment the biomaterial may be extracted at a pH of from about 2 to about 6. For example the pH during extraction may be about 2, about 3, about 4, about 5 or about 6. In one embodiment the pH is about 4.

In accordance with the present invention, after extraction, the solution containing the extracted biomaterial is then separated. In one embodiment the solution may be centrifuged so as to separate a supernatant from solid residue. In one embodiment the solution may be centrifuged for period of time, the length of which is proportional to the speed of centrifuging and may range from several minutes to a few hours until separation is achieved. For example the solution may be centrifuged for about 5, about 10, about 15, about 30, about 45 minutes or about 1, about 2, about 3 or more hours. The solution may be centrifuged at a speed of at least about 200 rpm up to the maximum equipment speed, for example about 60000 rpm. For example the solution may be centrifuged at a speed of about 2000, about 3000, about 4000, about 5000, about 6000, about 7000, about 8000, about 9000, about 10000, about 20000, about 30000, about 40000, about 50000 or about 60000 rpm. For example the solution may be centrifuged for about 3 hours, at about 4000 RPM. In one embodiment the supernatant may comprise a transparent, jelly-like solution.

In one embodiment, prior to centrifuging and where the solution is highly viscous, the solution may be diluted with additional acid using the same type and concentration of acid used in the original mixing solution, for example, 100 mM acetic acid). Addition of additional acid may improve the flow for easier handling. Alternatively, a different acidic solution may be added.

In another embodiment the solution containing the extracted biomaterial may be separated by another chemical or physical separation process. For example the solution containing the extracted biomaterial may be separated by filtration whereby the solubilsed biomaterial will be contained in the filtrate.

In accordance with the present invention, after separation, the separated solution is then freeze-dried at a rate sufficient to enable the biomaterial to be isolated. In one embodiment the rate is sufficient to enable substantially all or all of the solvent to be sublimated leaving the biomaterial as a purified product residue. In one embodiment any fat or other contaminants on the surface of the supernatant may be removed prior to freeze-drying. In one embodiment, during centrifuging fat may separate out into a layer which may be removed by physical means such as by skimming or decanting. Freeze-drying may be continued until a dry foam is obtained and substantially all water in the sample has sublimated. The dry foam may be suitably white in colour.

In one embodiment the freeze-drying step may involve firstly an equilibration step in which the collagen mixture is held at a temperature of about 10 to about 30° C., for example for about 15, about 20 or about 25° C. for a period of 0 to up to about 60 minutes, for example for about 10, about 15, about 20, about 25, about 30, about 35, about 40, about 45, about 50 or about 55 minutes. The collagen mixture may then be suitably cooled at a ramp rate range from less than about 1° C./min to about 50°/min, for example at a ramp rate of about 0.1, about 0.5, about 1, about 5, about 10, about 15, about 20, about 25, about 30, about 35, about 40 or about 45° C./min to a final temperature in the range of about −5° C. to about −80° C., for example, about −10, about −20, about −30, about −40, about −50, about −60 or about −70° C. In one embodiment the ramp rate is about 5° C./min. The ramp rate that may be used is dependent on the biological material being isolated. When collagen is isolated, the ramp rate for cooling may be between 0.5 to 5° C./min however, a faster or slower rate may be use depending on the amount and distribution of impurities. The temperature may be held at the final temperature for about 5 mins or longer, for example, for about 12 hours. The length of time depends on the volume and size of the solution, the length of time suitably being sufficient for the solution to freeze completely and the final temperature to equilibrate to the same level through the frozen solution. The freeze-dryer used may be set up so that the condenser temperature is suitably between about 0° C. and about −105° C., for example between about −40 and about −75° C. The vacuum in the freeze-dryer used may be pulled until it is between about 4.58 to about 0.005 torr (about 0.61 kPa- about 0.00067 kPa), typically between about 0.15 to about 0.035 torr (about 0.012- about 0.0047 kPa). Any remaining impurities which separate out to the surface of the foam may be removed from the purified collagen suitably by physical separation of the impurity layer.

The extracted biomaterial may be cross-linked for example using a cross-linking agent such as EDC, before or after freeze-drying.

The present invention provides at least in preferred embodiments, a method of extracting and purifying a biomaterial extract which involves less steps than those of conventional processes using less harsh chemicals or processing steps.

In the present invention the extraction conditions may be optimized so as to produce collagen of commercial quality in large quantities at lower cost. In one embodiment the process does not involve the addition of a salt to precipitate the collagen prior to freezing and may not require the addition of proteases or enzymes to assist in collagen extraction. Collagen of quality equivalent to currently commercially sold collagen may be extracted by the method of the invention as disclosed herein using freeze-drying as the purifying process. Freeze-drying is a low-temperature purification process that does not disrupt the physical structure of collagen. By use of freeze-drying, the product suffers less modification to the chemical structure of collagen since harsh chemical solvents and temperatures in the range of 50 to 60° C. may be avoided. The process of the invention may be cheaper than conventional processes, particularly by use of existing by-products from in vivo experiments. The process of the invention may be readily scaled up.

Conventional processes for obtaining collagen do not use freeze-drying in order to purify the collagen in the manner as described in the present invention.

The present invention also relates to a biomaterial extract prepared by the process of the invention.

The product of the invention may be used in methods and applications as referred to herein in the Background of the Invention. The product of the invention may be used in cosmetic, medical, pharmaceutical, food or veterinarial applications and may be applied topically, intravenously, intramuscularly, intravascularly, intraperitoneally, subcutaneously or orally.

The product of the invention may be used as an addition to new materials as a coating or incorporation into a material in order to make it more biocompatible such as for soft tissue replacement, wound covering, as a drug delivery matrices or for bone or cartilage remodeling, or as a substrate for cell growth. Other applications include biological coatings/films/membranes, fillers/sealants, hemostats, fibers, fabric meshes, tubes for tendon/ligament/nerve devices, injectable systems, cosmetics, artificial skin, healing dressings, bone-reconstruction materials, scaffolds, sutures, arterial vessel replacements, vitreous replacements, endodontic therapy.

The product of the invention may be used in preparation of creams, ointments, films, bags, fibres, composites, suspensions, tablets, capsules, delayed release capsules, implants, foams, active ingredient carriers, parenterals, enterals, eye drops, nanocapsules, as carriers, sponges or fleece.

The biomaterial may be used together with another active such as antiinflammatories, antihistamines, antiallergics, disinfectants, antimicrobials, growth factors, anti-dehydration compounds, antiseptics or other compounds suitably for medical or veterinary uses.

EXAMPLES

The present invention will now be described by way of example. The examples should not be construed as in any way limiting the scope of the invention.

Example 1

Freshly obtained, shaven skin of post-sacrificed animals (rat or rabbit) from in vivo studies was immediately stored in a deep freeze and kept until use.

The skin was cut into 1 to 3 mm pieces and soaked for up to two weeks in a 95% alcohol solution so as to disinfect the skin and dehydrate it. The skin was then placed into a beaker containing 1:1000 acetic acid solution and stirred for 4 to 14 days. The solution was then centrifuged for 3 hours at 4,000 RPM to separate the transparent, jelly-like solution from the remaining solid residue. Prior to centrifuging, when the solution was highly viscous, the solution was diluted with additional 100 mM acetic acid. The supernatant was then transferred into vessels for freeze-drying. Prior to freeze-drying any fat on the surface of the supernatant was removed. In this regard fat separates out into a layer during centrifuging and can be removed by physical means such as skimming or decanting. Freeze-drying was conducted using ramp rates previously described until a dry white foam was obtained. Any remaining impurities separate out of the surface of the foam and can be removed by physical separation of the impurity layer.

Example 2

A test was conducted to determine whether the product produced by the method of the present invention is comparable in material characteristics with a commercial quality Type 1 Collagen. FTIR (Fourier transform infrared spectroscopy) was conducted on the product of the invention and a commercial-quality collagen, Collagen-Type 1—Bovine Tendon-Sigma fibers supplied by Sigma. The results of the FTIR are shown in FIG. 1. In addition a chemical cross-linking reaction was performed on both the product of the invention and the commercial collagen to test whether the product of the invention responds in the same manner as commercial quantity collagen. The cross-linking mechanism is proposed as follows:

1-ethyl-3-(3-dimethylaminopropyl)carbodiimide/N-hydroxysuccinimide (EDC/NHS) cross-linking mechanism

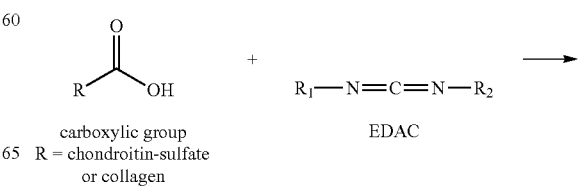

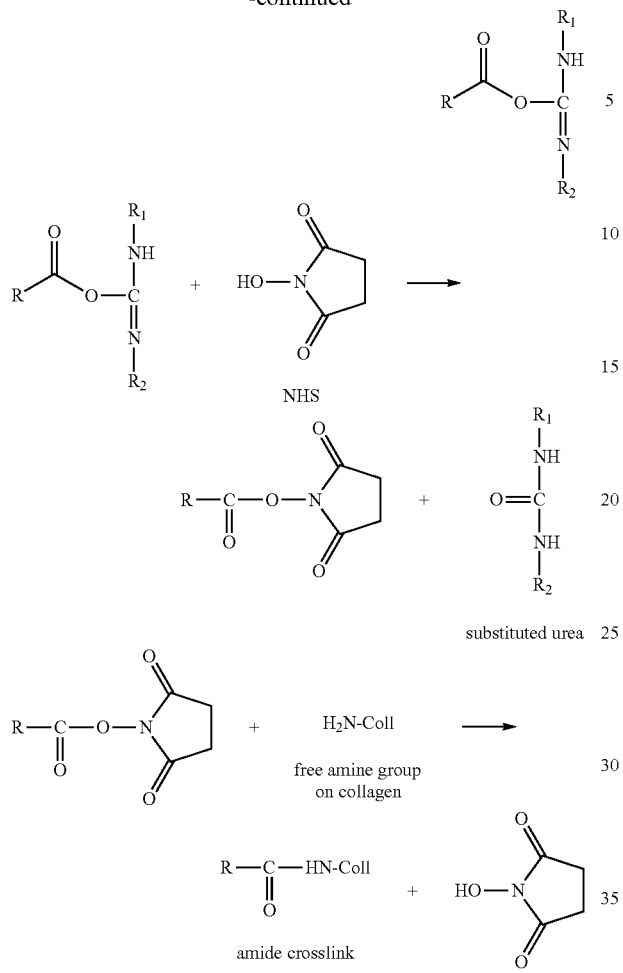

The resulting cross-linked products were examined by Fourier-transform infrared (FTIR) spectroscopy. The results of the FTIR spectroscopy are also shown in FIG. 1.

It can be seen from FIG. 1 that the FTIR profile of the product of the invention matches that of the commercial collagen. In addition, the cross-linking reaction affected the FTIR spectra of both the product of the invention and the commercial collagen in the same way. FIG. 1 indicates that the chemical structure of the collagen product of the present invention is equivalent to that of commercial collagen.

Example 3

Basic cell culture tests were conducted. Cell morphology was observed using light microscopy. Cell proliferation rate and metabolic activity was measured using the MTT (yellow tetrazolium) cell proliferation assay. The basic cell culture tests indicate that the product of the invention is non-toxic to cells and can support cell growth to an extent equivalent to that of commercial collagen.

INDUSTRIAL APPLICABILITY

The present invention relates to a process for extracting a biomaterial such as collagen. The product of the invention may be used in cosmetic, medical, pharmaceutical, food or veterinarial industries.

Other embodiments of the invention will be apparent to those skilled in the art from consideration of the specification and practice of the invention disclosed herein.

The invention claimed is:

1. A process for isolating collagen from biological tissue comprising:
    contacting the tissue with an extracting solution so as to extract collagen into solution;
    separating a solution containing the collagen by centrifuging or by filtration;
    removing fat and other contaminants from the surface of the separated solution directly prior to freeze-drying the separated solution and freeze-drying the separated solution at a rate sufficient to enable the collagen to be isolated.

2. A process according to claim 1, wherein the biological tissue is fetal tissue, skin/dermis tissue, muscle or connective tissue.

3. A process according to claim 2, wherein the biological tissue is animal skin.

4. A process according to claim 3, wherein the animal skin is skin of a rat, rabbit, goat, cow or pig.

5. A process according to claim 1, wherein the collagen is collagen Type 1.

6. A process according to claim 1, wherein the extracting solution is an acidic solution, a pH neutral solvent, an organic acid buffer, a Tris-HCl buffer or alkali-containing buffer system.

7. A process according to claim 6, wherein the acidic solution is an acetic acid solution.

8. A process according to claim 1, wherein the freeze-drying is performed at a cooling rate of less than 1° C/min to 50° C/min.

9. A process according to claim 1, wherein the freeze-drying is performed at a cooling rate of between 0.5° C/min to 5° C/min.

10. A process according to claim 1, wherein the extracted collagen is further cross-linked before or after freeze-drying.

11. A process according to claim 1, wherein the freeze-drying is performed at a cooling rate of less than 0.1° C/min to 50° C/min.

* * * * *